(12) United States Patent
Betzold et al.

(10) Patent No.: US 7,599,740 B2
(45) Date of Patent: Oct. 6, 2009

(54) VENTRICULAR EVENT FILTERING FOR AN IMPLANTABLE MEDICAL DEVICE

(75) Inventors: Robert A. Betzold, Fridley, MN (US); David A. Casavant, Reading, MA (US); Paul A. Belk, Maple Grove, MN (US); Thomas J. Mullen, Ham Lake, MN (US); John C. Stroebel, Blaine, MN (US); Steven R. Hornberger, Minneapolis, MN (US); Todd J. Sheldon, North Oaks, MN (US); Douglas A. Peterson, Apple Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 346 days.

(21) Appl. No.: 11/748,659

(22) Filed: May 15, 2007

(65) Prior Publication Data

US 2007/0213777 A1 Sep. 13, 2007

Related U.S. Application Data

(60) Division of application No. 10/850,666, filed on May 21, 2004, now Pat. No. 7,245,966, which is a continuation-in-part of application No. 10/246,816, filed on Sep. 17, 2002, now Pat. No. 7,130,683, which is a continuation-in-part of application No. 09/746,571, filed on Dec. 21, 2000, now Pat. No. 6,772,005.

(51) Int. Cl.
*A61N 1/362* (2006.01)

(52) U.S. Cl. ........................................ 607/9
(58) Field of Classification Search .............. 607/9, 607/14, 27; 128/901
See application file for complete search history.

(56) References Cited

U.S. PATENT DOCUMENTS

| | | | |
|---|---|---|---|
| 3,057,356 A | 10/1962 | Greatbatch |
| 3,253,596 A | 5/1966 | Keller |
| 3,478,746 A | 11/1969 | Greatbatch |
| 3,595,242 A | 7/1971 | Berkovits |
| 3,648,707 A | 3/1972 | Greatbatch |
| 3,747,604 A | 7/1973 | Berkovits |
| 4,312,355 A | 1/1982 | Funke |
| 4,386,610 A | 6/1983 | Leckrone |
| 4,428,378 A | 1/1984 | Anderson et al. |
| 4,432,362 A | 2/1984 | Leckrone et al. |
| 4,476,868 A | 10/1984 | Thompson |
| 4,523,593 A | 6/1985 | Rueter et al. |
| 4,577,633 A | 3/1986 | Berkovits et al. |
| 4,587,970 A | 5/1986 | Holley et al. |
| 4,726,380 A | 2/1988 | Vollmann et al. |

(Continued)

FOREIGN PATENT DOCUMENTS

EP 0363015 4/1990

(Continued)

*Primary Examiner*—Carl H. Layno
*Assistant Examiner*—Jon-Eric C. Morales
(74) *Attorney, Agent, or Firm*—Stephen W. Bauer

(57) ABSTRACT

Pacing parameters are provided to address cross talk and intrinsic ventricular events occurring within a predefined blanking period following an atrial event. The parameters are used in conjunction with protocol for minimizing or reducing ventricular pacing, wherein ignoring intrinsic ventricular events during the blanking period might otherwise affect the performance of the protocol.

2 Claims, 12 Drawing Sheets

U.S. PATENT DOCUMENTS

| | | | |
|---|---|---|---|
| 4,727,877 A | 3/1988 | Kallok | |
| 4,856,523 A | 8/1989 | Sholder et al. | |
| 4,856,524 A | 8/1989 | Baker | |
| 4,880,005 A | 11/1989 | Pless et al. | |
| 4,890,617 A | 1/1990 | Markowitz et al. | |
| 4,932,046 A | 6/1990 | Katz et al. | |
| 4,941,471 A | 7/1990 | Mehra | |
| 4,953,551 A | 9/1990 | Mehra et al. | |
| 5,052,388 A | 10/1991 | Sivula et al. | |
| 5,085,215 A | 2/1992 | Nappholz et al. | |
| 5,097,832 A | 3/1992 | Buchanan | |
| 5,117,824 A | 6/1992 | Keimel et al. | |
| 5,133,350 A | 7/1992 | Duffin | |
| 5,144,950 A | 9/1992 | Stoop et al. | |
| 5,163,427 A | 11/1992 | Keimel | |
| 5,188,105 A | 2/1993 | Keimel | |
| 5,188,117 A | 2/1993 | Steinhaus et al. | |
| 5,228,438 A | 7/1993 | Buchanan | |
| 5,273,035 A | 12/1993 | Markowitz et al. | |
| 5,292,340 A | 3/1994 | Crosby et al. | |
| 5,318,594 A | 6/1994 | Limousin et al. | |
| 5,334,220 A | 8/1994 | Sholder | |
| 5,345,362 A | 9/1994 | Winkler | |
| 5,372,607 A | 12/1994 | Stone et al. | |
| 5,388,586 A | 2/1995 | Lee et al. | |
| 5,417,714 A | 5/1995 | Levine et al. | |
| 5,522,859 A | 6/1996 | Stroebel et al. | |
| 5,540,725 A | 7/1996 | Bornzin et al. | |
| 5,584,868 A | 12/1996 | Salo et al. | |
| 5,591,214 A | 1/1997 | Lu | |
| 5,626,623 A | 5/1997 | Kieval et al. | |
| 5,643,326 A | 7/1997 | Weiner et al. | |
| 5,658,320 A * | 8/1997 | Betzold et al. | 607/14 |
| 5,674,257 A | 10/1997 | Stroebel et al. | |
| 5,697,958 A | 12/1997 | Paul et al. | |
| 5,725,561 A | 3/1998 | Stroebel et al. | |
| 5,741,308 A | 4/1998 | Sholder et al. | |
| 5,814,077 A | 9/1998 | Levine et al. | |
| 5,836,974 A | 11/1998 | Christini et al. | |
| 5,861,007 A | 1/1999 | Hess et al. | |
| 5,873,895 A | 2/1999 | Sholder et al. | |
| 5,954,755 A | 9/1999 | Casavant | |
| 5,999,850 A | 12/1999 | Dawson et al. | |
| 6,058,326 A | 5/2000 | Hess et al. | |
| 6,122,546 A | 9/2000 | Levine et al. | |
| 6,128,529 A | 10/2000 | Esler et al. | |
| 6,128,534 A | 10/2000 | Park et al. | |
| 6,141,586 A | 10/2000 | Mower | |
| 6,169,918 B1 | 1/2001 | Haefner et al. | |
| 6,198,968 B1 | 3/2001 | Prutchi et al. | |
| 6,256,541 B1 | 7/2001 | Heil et al. | |
| 6,321,115 B1 | 11/2001 | Mouchawar et al. | |
| 6,397,105 B1 | 5/2002 | Bouhour et al. | |
| 6,434,424 B1 | 8/2002 | Igel et al. | |
| 6,477,416 B1 * | 11/2002 | Florio et al. | 607/9 |
| 6,609,028 B2 | 8/2003 | Struble | |
| 6,654,637 B2 | 11/2003 | Rouw et al. | |
| 6,697,673 B1 | 2/2004 | Lu | |
| 6,731,980 B1 | 5/2004 | Mouchawar et al. | |
| 6,772,005 B2 | 8/2004 | Casavant et al. | |
| 6,792,307 B1 | 9/2004 | Levine et al. | |
| 6,873,875 B1 | 3/2005 | Gilkerson et al. | |
| 6,904,315 B2 | 6/2005 | Panken et al. | |
| 6,925,326 B1 | 8/2005 | Levine et al. | |
| 6,978,175 B1 | 12/2005 | Florio et al. | |
| 7,027,868 B2 | 4/2006 | Rueter et al. | |
| 7,123,960 B2 | 10/2006 | Ding et al. | |
| 7,130,683 B2 | 10/2006 | Casavant et al. | |
| 7,218,965 B2 | 5/2007 | Casavant et al. | |
| 7,245,966 B2 | 7/2007 | Betzold et al. | |
| 7,248,924 B2 | 7/2007 | Casavant | |
| 7,254,441 B2 | 8/2007 | Stroebel | |
| 7,283,872 B2 | 10/2007 | Boute et al. | |
| 2002/0038482 A1 | 4/2002 | Mennicke et al. | |
| 2002/0041700 A1 | 4/2002 | Therbaud | |
| 2002/0082646 A1 | 6/2002 | Casavant et al. | |
| 2002/0128687 A1 | 9/2002 | Baker et al. | |
| 2002/0138417 A1 | 9/2002 | Lawrence | |
| 2003/0078627 A1 | 4/2003 | Casavant et al. | |
| 2004/0010292 A1 | 1/2004 | Amblard et al. | |
| 2004/0024694 A1 | 2/2004 | Lawrence et al. | |
| 2004/0078321 A1 | 4/2004 | Lawrence | |
| 2004/0117316 A1 | 6/2004 | Gillum | |
| 2004/0260349 A1 | 12/2004 | Stroebel | |
| 2005/0038482 A1 | 2/2005 | Yonce et al. | |
| 2005/0055059 A1 | 3/2005 | Betzold et al. | |
| 2005/0096708 A1 | 5/2005 | Seim et al. | |
| 2005/0177197 A1 | 8/2005 | Betzold | |
| 2005/0267539 A1 | 12/2005 | Betzold et al. | |
| 2005/0273430 A1 | 12/2005 | Pliha | |
| 2007/0203523 A1 | 8/2007 | Betzold | |
| 2007/0213777 A1 | 9/2007 | Betzold et al. | |

FOREIGN PATENT DOCUMENTS

| | | |
|---|---|---|
| EP | 0448193 | 9/1991 |
| EP | 0624386 | 11/1994 |
| EP | 0830877 | 3/1998 |
| EP | 1449562 | 8/2004 |
| WO | WO 95/32758 | 12/1995 |
| WO | WO 02/051499 | 7/2002 |
| WO | WO 2005/097259 | 10/2005 |
| WO | WO 2005/113065 | 12/2005 |
| WO | WO 2006/079037 | 7/2006 |
| WO | WO 2006/079066 | 7/2006 |

* cited by examiner

FIG. 10A
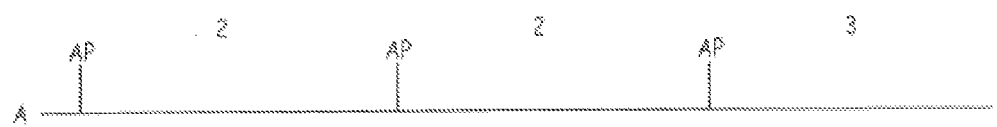
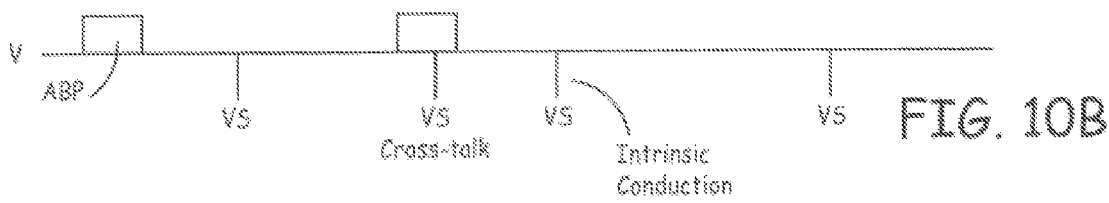
FIG. 10B

VENTRICULAR EVENT FILTERING FOR AN IMPLANTABLE MEDICAL DEVICE

CROSS REFERENCE TO RELATED APPLICATIONS

The present application is a divisional application of Ser. No. 10/850,666, filed May 21, 2004, now U.S. Pat. No. 7,245,966, which is a continuation-in-part of Ser. No. 10/246,816, filed Sep. 17, 2002, now U.S. Pat. No. 7,130,683 which is a continuation-in-part of non-provisional U.S. patent application Ser. No. 09/746,571 filed Dec. 21, 2000, now U.S. Pat. No. 6,772,005 both of which are herein incorporated by reference in their entireties.

FIELD OF THE INVENTION

The present invention generally relates to implantable medical devices and more specifically to implantable medical devices for providing cardiac pacing.

BACKGROUND OF THE INVENTION

In a wide variety of commonly employed dual chamber pacing modalities, cross-talk could cause one or more errors. For example, a paced atrial event may be sensed by a ventricular lead and misinterpreted as a ventricular event. This would effectively be far field sensing of an atrial pace. This typically would not be a problem with intrinsic atrial depolarizations, due to their lower magnitude. Conversely, far field sensing of intrinsic R waves or paced ventricular events could likewise be misinterpreted if sensed by an atrial lead.

To account for such errors, various blanking or refractory periods are employed such that these events are either not sensed or are simply ignored. In dealing with far field sensing of atrial-paced events, ventricular events that are sensed during a given window following the atrial pace are ignored. Depending upon the application, this window may be referred to as the atrial blanking period (ABP) or some similar nomenclature. Through clinical application, practitioners have determined that if such far field sensing is going to occur, it typically happens within 80 ms or less of the original event (e.g., the atrial pace). Thus, this window is conservatively set at 80 ms or so, depending upon the specific device or the manufacturer.

In use, such as in a DDD mode, providing this window adequately addresses the cross-talk problem and generally does not create additional problems. Sometimes genuine intrinsic events will occur during the window and will also be ignored. For example, a premature ventricular contraction (PVC) is an intrinsic, conducted event but if it falls within the window it will be ignored.

Whether a far field sense or an intrinsic event, such as a PVC, occurs and is ignored, the subsequent action of the device in typical dual chamber modes is to provide a ventricular pace at the expiration of a predetermined interval following the initial atrial event, unless inhibited. If the ignored event was cross talk, it is certainly possible that a subsequent intrinsic ventricular event will occur and inhibit the pace. Alternatively, for any number of reasons no intrinsic event will occur during the atrial-ventricular interval (AVI) and the ventricular pace is delivered. If the ignored event was a PVC, it is quite likely that there will not be another intrinsic ventricular event in the current A-A interval and the device will deliver a pacing pulse at the expiration of the AVI.

Thus, the use of such a window in dual chamber devices is appropriate to prevent cross talk without introducing additional problematic results. As disclosed in the above referenced applications, a mode and/or protocol is provided that minimizes or greatly reduces ventricular pacing and is referred to as MVP. In summary, MVP tolerates a complete cycle (A-A) interval without ventricular activity, in order to promote intrinsic conduction. In many patients, the conduction pathway is intact but is delayed beyond the capabilities of traditional dual chamber mode timing. Thus, ventricular pacing is provided when not absolutely necessary and this is believed to be undesirable.

Various embodiments of MVP are described in greater detail in the referenced applications, but the mode generally operates by monitoring a complete cycle for intrinsic conduction. If intrinsic conduction fails and no ventricular event occurs, ventricular pacing is provided in the subsequent cycle.

The use of the above described window (ABP) presents a challenge to this minimized or reduced ventricular pacing mode. For example, if true cross talk occurs and is ignored, subsequent operation continues unhindered. However, if a PVC occurs during this window, it is ignored. Thus, a true intrinsic ventricular event is being ignored by a mode that bases it subsequent operation on the presence or absence of intrinsic ventricular activity during a given cycle. If a PVC occurs during this window it is ignored; assuming no other ventricular activity occurs during this interval, which is quite possible, the device determines that the current A-A interval is devoid of intrinsic ventricular conduction. Subsequently, the device mode switches or otherwise operates to deliver ventricular pacing in a subsequent cardiac cycle and depending upon the embodiment, one or more subsequent cycles. While not in and of itself harmful, this ventricular pacing is generally not necessary as intact conduction exists. As a result, PVC's may operate to reduce the efficiency of the ventricular minimization or reduction protocol insomuch as that efficiency is determined to be the reduction or elimination of otherwise unnecessary ventricular pacing. This may simply result in a relatively low number of unnecessary ventricular paces. Alternatively, depending upon the specific embodiment of MVP, a series of PVCs may be interpreted as a loss of conduction that prevents a return to the atrial based mode for a longer period of time.

BRIEF DESCRIPTION OF THE DRAWINGS

FIGS. 10A-10B are ladder diagrams that illustrate ventricular sense events during an ABP.

DETAILED DESCRIPTION OF THE DRAWINGS

Figure 1:
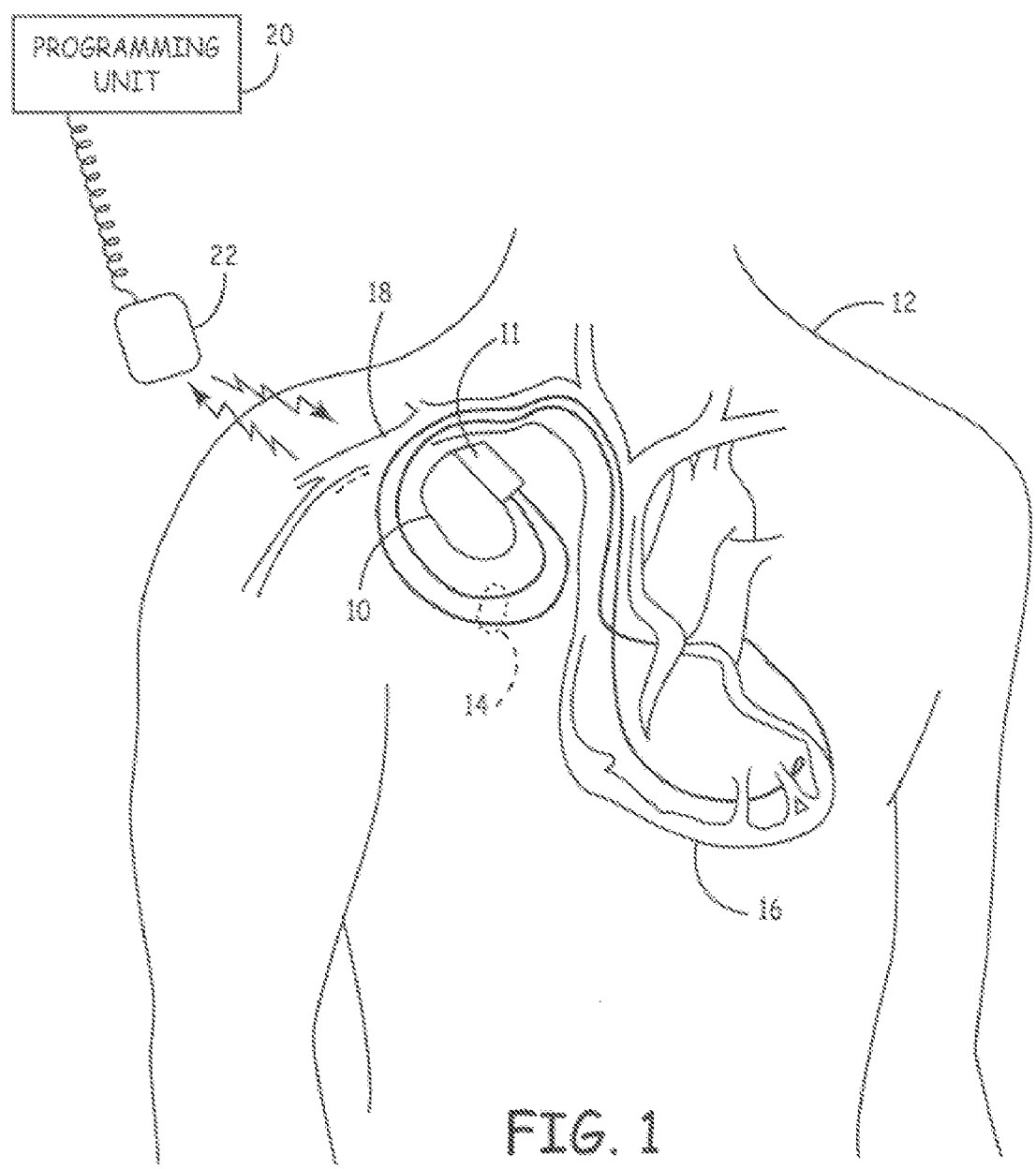
FIG. 1 is an illustration of a body-implantable device system in accordance with the present invention, including a hermetically sealed device implanted in a patient and an external programming unit.

FIG. 1 is an illustration of an implantable medical device system adapted for use in accordance with the present invention. The medical device system shown in FIG. 1 includes an implantable device 10—a pacemaker in this embodiment—that has been implanted in a patient 12. In accordance with conventional practice in the art, pacemaker 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with its distal end situated in the atrium and/or ventricle of heart 16.

Although the present invention will be described herein in one embodiment which includes a pacemaker, those of ordinary skill in the art having the benefit of the present disclosure will appreciate that the present invention may be advantageously practiced in connection with numerous other types of implantable medical device systems, and indeed in any application in which it is desirable to provide the preferred ADI/R pacing mode (i.e., the MVP modality), as may occur in ICDs and the like.

Also depicted in FIG. 1 is an external programming unit 20 for non-invasive communication with implanted device 10 via uplink and downlink communication channels, to be hereinafter described in further detail. Associated with programming unit 20 is a programming head 22, in accordance with conventional medical device programming systems, for facilitating two-way communication between implanted device 10 and programmer 20. In many known implantable device systems, a programming head such as that depicted in FIG. 1 is positioned on the patient's body over the implant site of the device (usually within 2- to 3-inches of skin contact), such that one or more antennae within the head can send RF signals to, and receive RE signals from, an antenna disposed within the hermetic enclosure of the implanted device or disposed within the connector block of the device, in accordance with common practice in the art.

Figure 2:
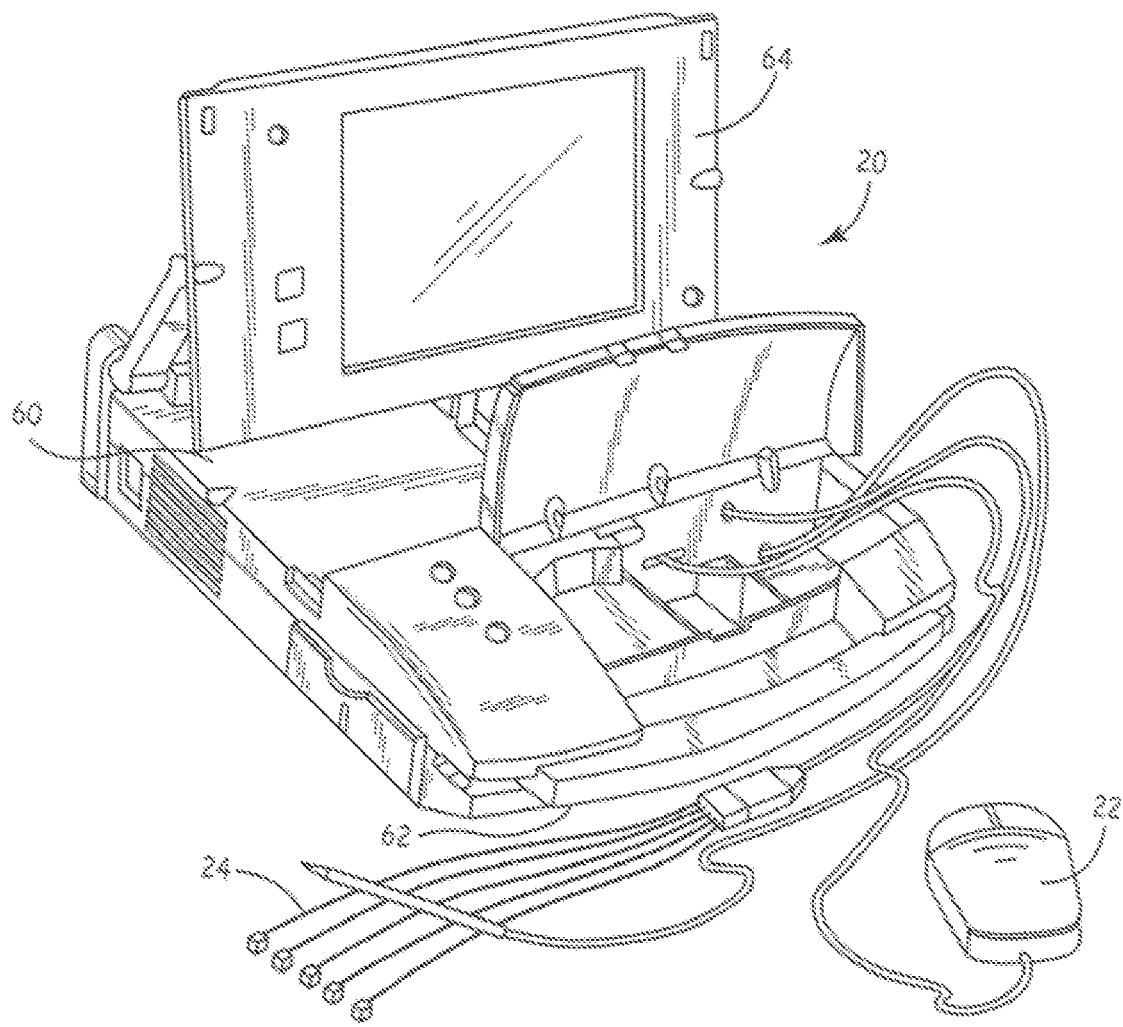
FIG. 2 is a perspective view of the external programming unit of FIG. 1.

FIG. 2 is a perspective view of programming unit 20 in accordance with the presently disclosed invention. Internally, programmer 20 includes a processing unit (not shown in the Figure) that in accordance with the presently disclosed invention is a personal computer type motherboard, e.g., a computer motherboard including an Intel Pentium 3 microprocessor and related circuitry such as digital memory. The details of design and operation of the programmer's computer system will not be set forth in detail in the present disclosure, as it is believed that such details are well known to those of ordinary skill in the art.

Referring to FIG. 2, programmer 20 comprises an outer housing 60, which is preferably made of thermal plastic or another suitably rugged yet relatively lightweight material. A carrying handle, designated generally as 62 in FIG. 2, is integrally formed into the front of housing 60. With handle 62, programmer 20 can be carried like a briefcase.

An articulating display screen 64 is disposed on the upper surface of housing 60. Display screen 64 folds down into a closed position (not shown) when programmer 20 is not in use, thereby reducing the size of programmer 20 and protecting the display surface of display 64 during transportation and storage thereof.

A floppy disk drive is disposed within housing 60 and is accessible via a disk insertion slot (not shown). A hard disk drive is also disposed within housing 60, and it is contemplated that a hard disk drive activity indicator, (e.g., an LED, not shown) could be provided to give a visible indication of hard disk activation.

As would be appreciated by those of ordinary skill in the art, it is often desirable 30 to provide a means for determining the status of the patient's conduction system. To accomplish this task and provide suitable ECG tracings, programmer 20 is equipped with external ECG leads 24.

In accordance with the present invention, programmer 20 is equipped with an internal printer (not shown) so that a hard copy of a patient's ECG or of graphics displayed on the programmer's display screen 64 can be generated. Several types of printers, such as the AR-100 printer available from General Scanning Co., are known and commercially available.

In the perspective view of FIG. 2, programmer 20 is shown with articulating display screen 64 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

As would be appreciated by those of ordinary skill in the art, display screen 64 is operatively coupled to the computer circuitry disposed within housing 60 and is adapted to provide a visual display of graphics and/or data under control of the internal computer. Programmer 20 described herein with reference to FIG. 2 is described in more detail in U.S. Pat. No. 5,345,362 issued to Thomas J. Winkler, entitled "Portable Computer Apparatus With Articulating Display Panel," which patent is hereby incorporated herein by reference in its entirety. The Medtronic Model 9790 programmer is the implantable device-programming unit with which the present invention may be advantageously practiced.

Figure 3:
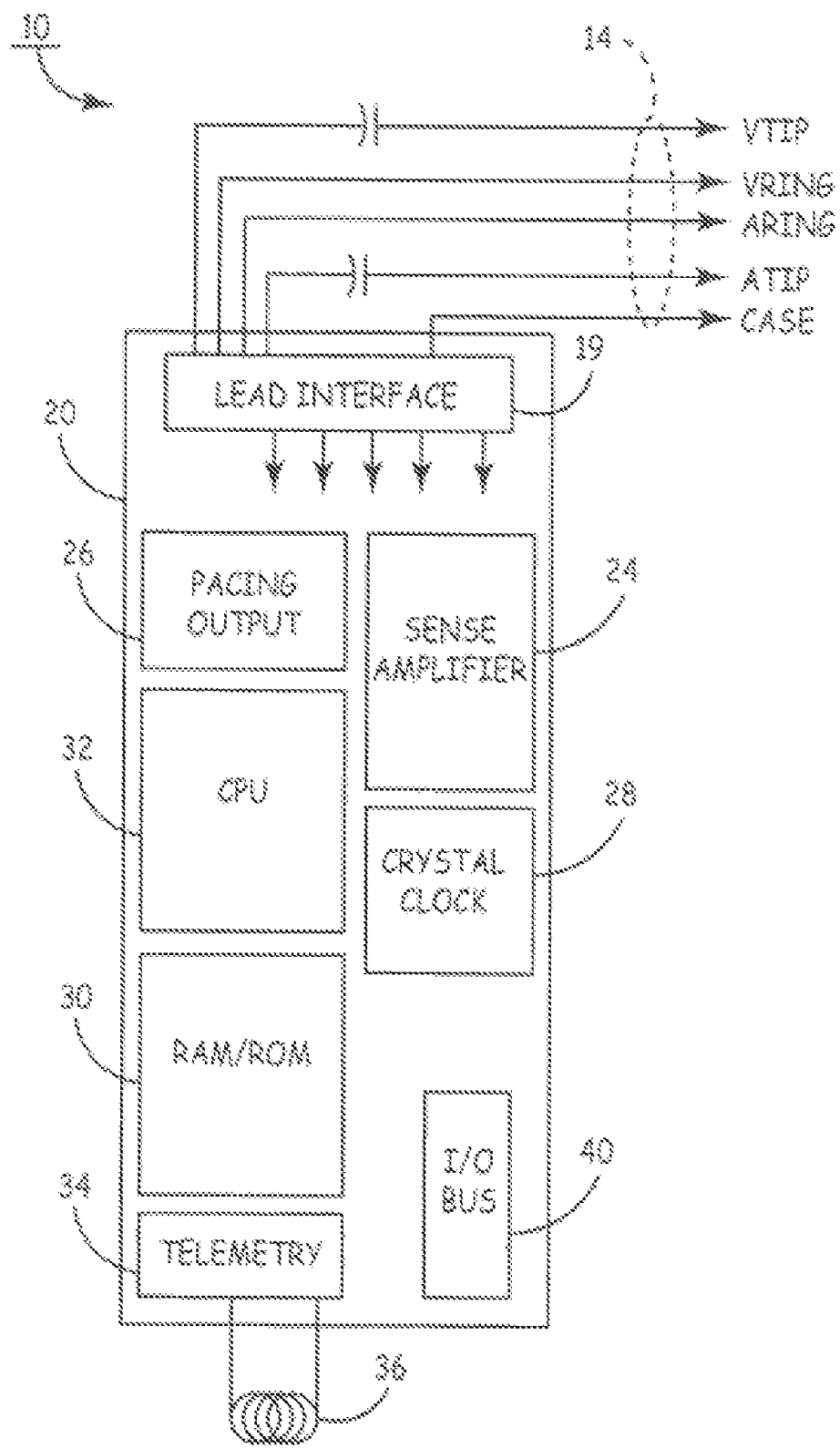
FIG. 3 is a block diagram of the implanted device from FIG. 1.

FIG. 3 is a block diagram of the electronic circuitry that makes up pulse generator 10 in accordance with the presently disclosed invention. As can be seen from FIG. 3, pacemaker 10 comprises a primary stimulation control circuit 20 for controlling the device's pacing and sensing functions. The circuitry associated with stimulation control circuit 20 may be of conventional design, in accordance, for example, with what is disclosed U.S. Pat. No. 5,052,388 issued to Sivula et al., "Method and apparatus for implementing activity sensing in a pulse generator." To the extent that certain components of pulse generator 10 are conventional in their design and operation, such components will not be described herein in detail, as it is believed that design and implementation of such components would be a matter of routine to those of ordinary skill in the art. For example, stimulation control circuit 20 in FIG. 3 includes sense amplifier circuitry 24, stimulating pulse output circuitry 26, a crystal clock 28, a random-access memory and read-only memory (RAM/ROM) unit 30, and a central processing unit (CPU) 32, all of which are well-known in the art.

Pacemaker 10 also includes internal communication circuit 34 so that it is capable communicating with external programmer/control unit 20, as described in FIG. 2 in greater detail.

With continued reference to FIG. 3, pulse generator 10 is coupled to one or more leads 14 which, when implanted, extend transvenously between the implant site of pulse generator 10 and the patient's heart 16, as previously noted with reference to FIG. 1. Physically, the connections between leads 14 and the various internal components of pulse generator 10 are facilitated by means of a conventional connector block assembly 11, shown in FIG. 1. Electrically, the coupling of the conductors of leads and internal electrical components of pulse generator 10 may be facilitated by means of a lead interface circuit 19 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of pulse generator 10, as would be familiar to those of ordinary skill in the art. For the sake of clarity, the specific connections between leads 14 and the various components of pulse generator 10 are not shown in FIG. 3, although it will be clear to those of ordinary skill in the art that, for example, leads 14 will necessarily be coupled, either directly or indirectly, to sense amplifier circuitry 24 and stimulating pulse output circuit 26, in accordance with common practice, such that cardiac electrical signals may be conveyed to sensing circuitry 24, and such that stimulating pulses may be delivered to cardiac tissue, via leads 14. Also not shown in FIG. 3 is the protection circuitry commonly included in implanted devices to protect, for example, the sensing circuitry of the device from high voltage stimulating pulses.

As previously noted, stimulation control circuit 20 includes central processing unit 32 which may be an off-the-shelf programmable microprocessor or micro controller, but in the present invention is a custom integrated circuit. Although specific connections between CPU 32 and other components of stimulation control circuit 20 are not shown in FIG. 3, it will be apparent to those of ordinary skill in the art that CPU 32 functions to control the timed operation of stimulating pulse output circuit 26 and sense amplifier circuit 24 under control of programming stored in RAM/ROM unit 30. It is believed that those of ordinary skill in the art will be familiar with such an operative arrangement.

With continued reference to FIG. 3, crystal oscillator circuit 28, in the presently preferred embodiment a 32,768-Hz crystal controlled oscillator provides main timing clock signals to stimulation control circuit 20. Again, the lines over which such clocking signals are provided to the various timed components of pulse generator 10 (e.g., microprocessor 32) are omitted from FIG. 3 for the sake of clarity.

It is to be understood that the various components of pulse generator 10 depicted 10 in FIG. 3 are powered by means of a battery (not shown) that is contained within the hermetic enclosure of pacemaker 10, in accordance with common practice in the art. For the sake of clarity in the Figures, the battery and the connections between it and the other components of pulse generator 10 are not shown.

Stimulating pulse output circuit 26, which functions to generate cardiac stimuli 15 under control of signals issued by CPU 32, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits that would be suitable for the purposes of practicing the present invention.

Sense amplifier circuit 24, which is of conventional design, functions to receive electrical cardiac signals from leads 14 and to process such signals to derive event signals reflecting the occurrence of specific cardiac electrical events, including atrial contractions (P-waves) and ventricular contractions (R-waves). CPU provides these event-indicating signals to CPU 32 for use in controlling the synchronous stimulating operations of pulse generator 10 in accordance with common practice in the art. In addition, these event-indicating signals may be communicated, via uplink transmission, to external programming unit 20 for visual display to a physician or clinician.

Those of ordinary skill in the art will appreciate that pacemaker 10 may include numerous other components and subsystems, for example, activity sensors and associated circuitry. The presence or absence of such additional components in pacemaker 10, however, is not believed to be pertinent to the present invention, which relates primarily to the implementation and operation of communication subsystem 34 in pacemaker 10, and an associated communication subsystem in external unit 20.

Figure 4:
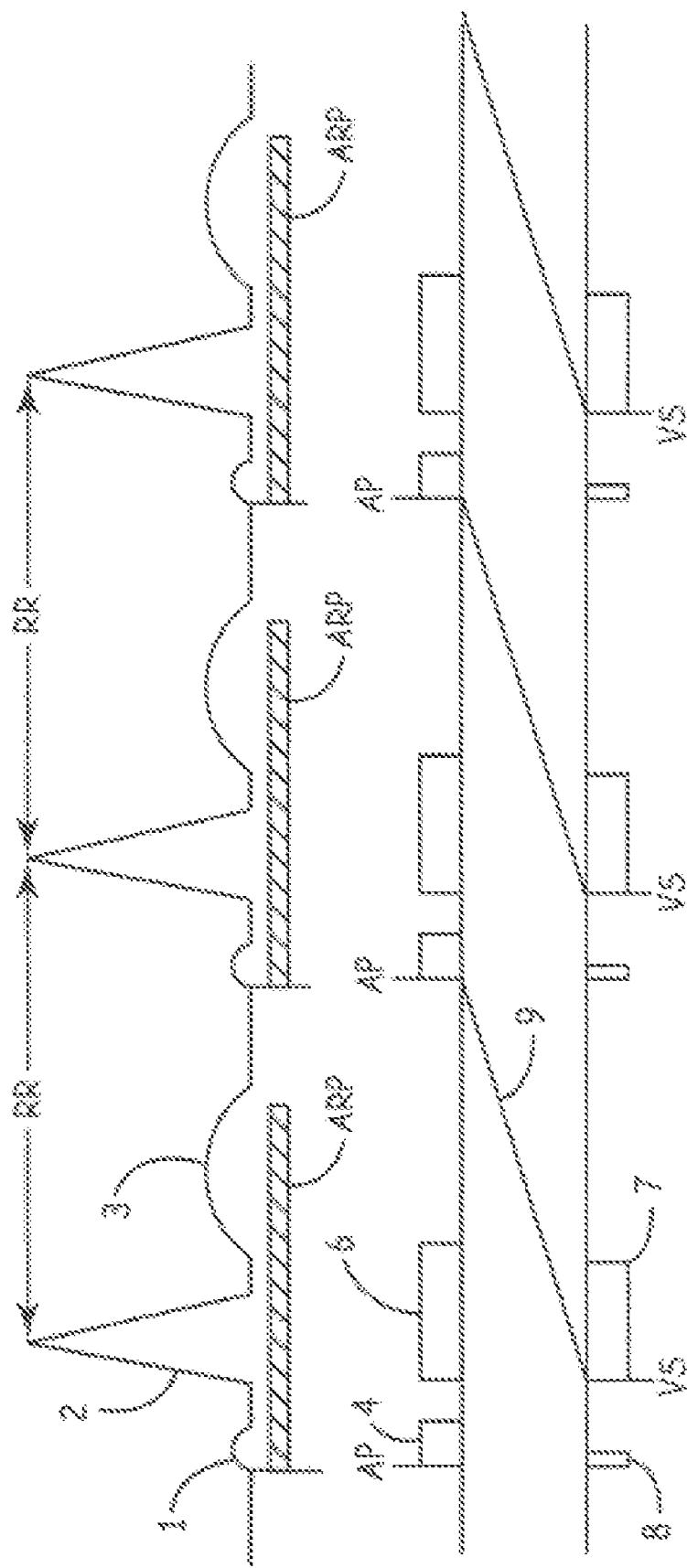
FIG. 4 is a ladder diagram of the ADI/R operation.

FIG. 4 is a ladder diagram of the ADI/R operation, specifically a Marker Channel® Diagram. With the help of the (pre-2002) NBG Code, one familiar with the state of the art will be able to discern that the letter in the first position (A) means that the pacemaker (or other implanted device) will pace the atrium in the absence of an atrial sensed event. The second letter (D) implies that the pacemaker will sense in dual chambers, that is, both the atrial and ventricular chambers. The third letter (I) means that, upon sensing in either chamber, pacing will be inhibited in that specific chamber. The final letter, R, implies that the device may be rate responsive that is, altering the atrial rate in response to an artificial sensor, such as a Piezo-electrical crystal, accelerometer, minute ventilation, etc.

The operation of the preferred ADI/R mode is depicted in the ladder diagram as follows. Atrial paced (or sensed) event 1 initiates a non-programmable, auto 15 adjusting (e.g., 100-150 millisecond) blanking period 4, followed by auto-adjusting atrial sensitivity (not shown). Sensing circuitry (see FIG. 3) determines if and when ventricular sensed event 2 has occurred. If detected, timing circuitry (see FIG. 3) initiates VA interval 9. Other timing, blanking periods, and refractory periods serve the following purposes. A programmable ventricular blanking period 8 prevents sensing of atrial pace 1 on the ventricular channel, sometimes termed "cross-talk." Ventricular sensed event 2 starts a 120 millisecond post ventricular atrial blanking (PVAB) period 6, followed by auto-adjusting atrial sensitivity. PVAB 6 serves the purpose of preventing sensing of the R-wave or T-wave on the atrial channel, termed "far-field R-wave sensing." Ventricular sensed event 2 also starts 100 millisecond ventricular blanking 7 followed by auto-adjusting ventricular sensitivity. This period serves the purpose of preventing sensing of the ventricular output pulse or the ventricular depolarization itself. Repolarization, or T-wave 3, follows R-wave 2. Ventricular event 2 detected by sensing circuitry (see FIG. 3) sends signal to timing circuitry to start VA interval 9, leading to the next atrial pacing cycle. Two R-R intervals are depicted in FIG. 4. As described in more detail hereinbelow, an ARP may have a nominal value of approximately seventy percent (70%) of a single preceding R-R interval (in a beat-to-beat implementation) or of a series of preceding R-R intervals.

Figure 5:
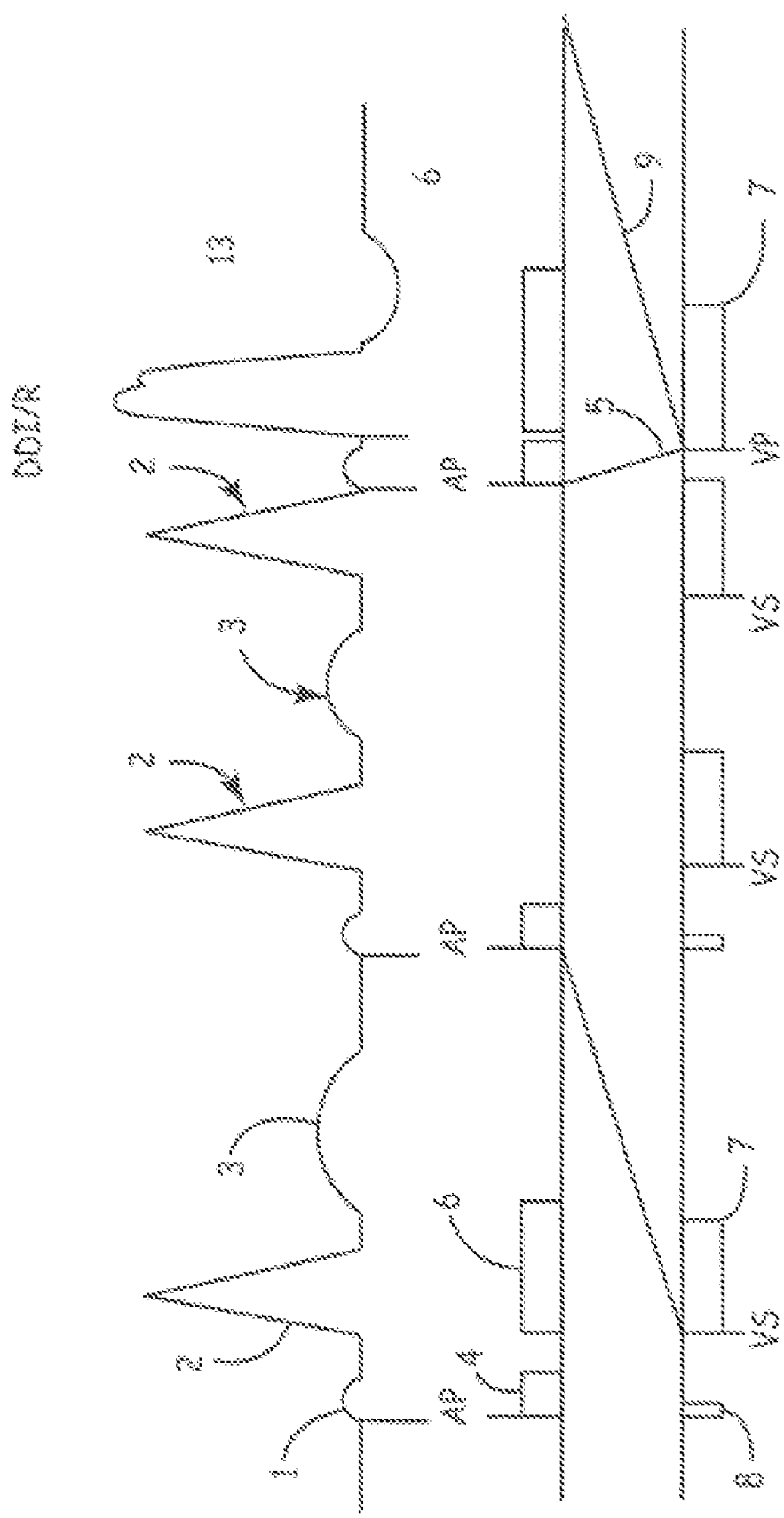
FIG. 5 is a ladder diagram of the committed DDD/R operation in the event that the patient develops transient AV block.

Taking into account that this mode would be used primarily with Sick Sinus patients who have full or some degree of intact AV conduction, this type of operation as depicted for the ADI/R mode is something the clinician or physician would expect to occur. In the presence of relatively reliable intact AV conduction the pacemaker will maintain the ADI/R operation/mode. Sensed ventricular events would occur in the vast majority of cardiac cycles (that is, PQRST). FIG. 5 teaches what will occur should the patient develop transient AV block for one or a few cardiac cycles.

FIG. 5 is a ladder diagram of the DDI/R operation in the event that the patient experiences a PVC, in one embodiment. The purpose of the DDI/R operation is to maintain ventricular support (i.e., help the patient recover sufficient cardiac output following the PVC). Briefly stated, the implanted device mode switches from the preferred ADI/R to the DDI/R for in response to a detected PVC for at least one cardiac cycle.

The timing of the DDI/R is as follows. In the DDI/R mode (third pacing cycle, labeled DDI/R), AV interval 5 is set to a short period (e.g., 80 milliseconds), following the paced P-wave due to the presence of a PVC between the second and third atrial paced events. The purpose of this short AV interval 5 is intended to suppress competition between ventricular pacing pulse culminating in paced R-wave 13 and any potential intrinsic R-wave with a delayed conduction from the previous paced atrial event. Assuming the presence of such an intrinsic R-wave, the timing of the ventricular output pulse would normally result in a ventricular pacing pulse falling into the absolute refractory period of the intrinsic, conducted R-wave, resulting in a psuedo-fusion beat (not shown). This operation is intended to prevent the onset of a ventricular tachycardia, should the ventricular pacing pulse fall into the relative refractory period of the ventricle, commonly called "pacing on T" phenomenon. In this respect, the reader is again cautioned that the drawings do not necessarily reflect actual or practical timing, but are intended to illustrate the notion of a mode switch (to DDI/R) following a PVC.

With respect to the foregoing, in one form of the invention, if the Ap encroaches on the preceding Vs (e.g. within 300 msec) for more than about four 30 depolarization events (e.g., consecutive beats), then the pacing rate is decreased. In effect, this creates a dynamic upper sensor rate. Thus, the present invention addresses an anticipated concerns with regard to the MVP modality providing relatively short VS-AP intervals. Such intervals could cause disadvantageous patient symptoms and may also have a negative heart remodeling effect. To counter these issues the MVP modality can operate such that after a V-Sense event (Vs), a scheduled A-Pace (Ap) event is delayed until some pre-defined interval expires. This aspect of the MVP modality is somewhat similar to upper tracking rate (UTR) hold off or non-competitive atrial pacing (NCAP) hold-off except that it is based on an A-Pace (Ap) event following a V-Sense (Vs). This results in the atrium being paced at a slightly lower rate than intended which may create issues that are known to exist with respect to so-called atrial overdrive pacing algorithms. This aspect of the MYP modality is preferably implemented in hardware (just like UTR and NCAP) primarily because of the critical timing involved.

In order to prevent adverse hemodynamics that may result from atrial pacing soon (e.g. within 250 msec) after a ventricular sense (i.e. Vp-As) while in the preferred ADI/R mode of pacing, one option is to (and subsequently limit for a period of time (e.g. one hour) the sensor driven pacing rate in the event of continuous cycles (e.g. 4-8 consecutive) of atrial pacing within a programmable interval (e.g. 250 msec) of the preceding R-waves. For example, such a dynamic upper rate limit is preferably set so that the Vs-Ap interval does not decrease to less than about 300 ms.

Continuing with the timing in FIG. 5, paced R-wave 13 starts a 120 millisecond ventricular blanking period 7, followed by auto adjusting ventricular sensitivity (not shown). Paced R-wave 13 also starts a 120 millisecond PVAB 6 followed by auto adjusting atrial sensitivity (not shown). Assuming the transient AV block self-corrects and a sensed R-wave is detected in response to the ventricular pace (Vp), the preferred ADI/R resumes with the next paced or sensed P-wave, as is depicted in FIG. 4.

Figure 6:
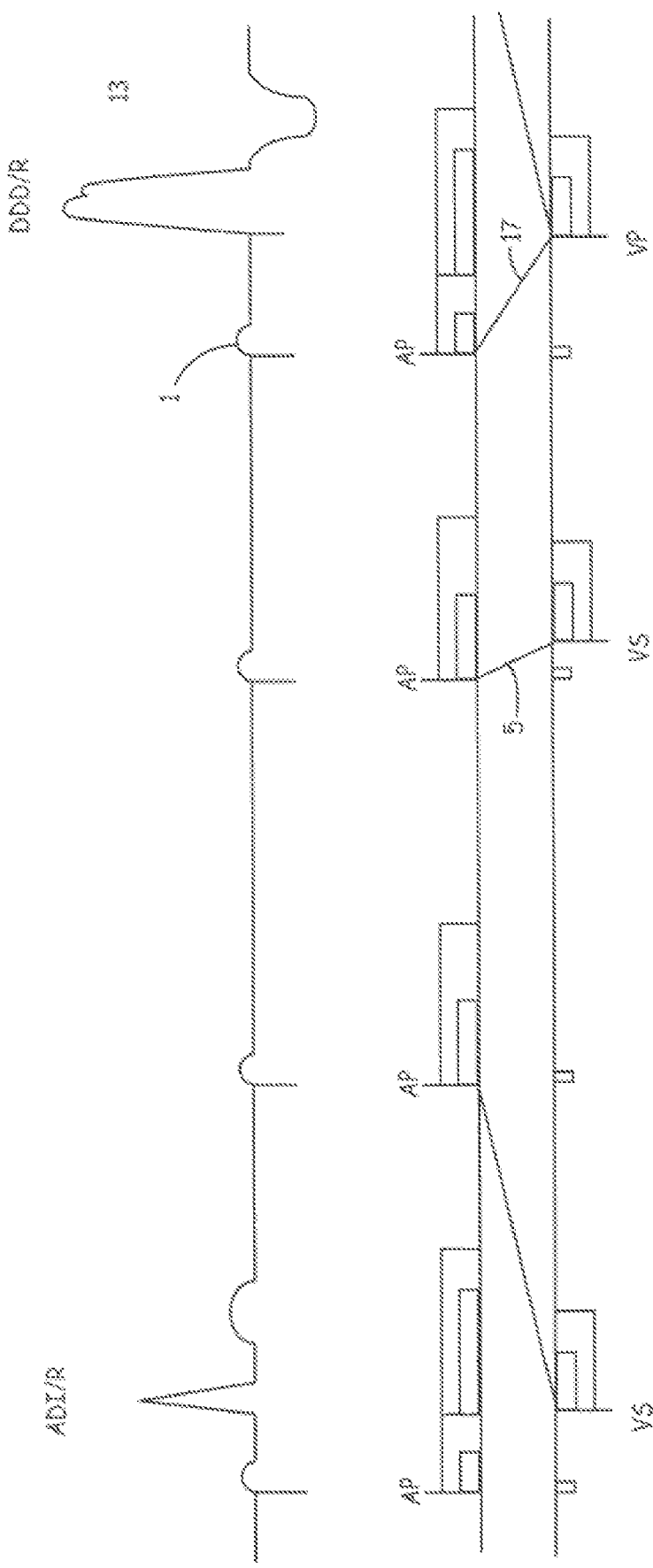
FIG. 6 is a ladder diagram that depicts the pacing operation in the event that the patient develops AV block that persists for more than one cycle.
Figure 7:
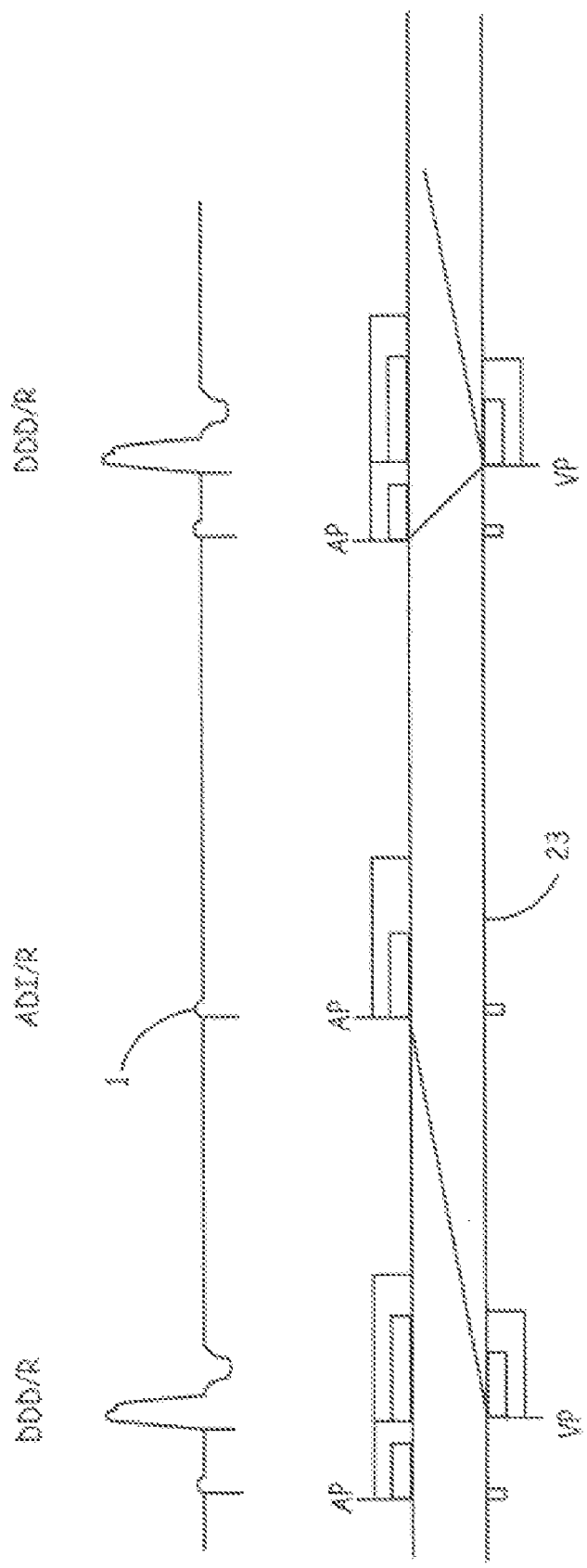
FIG. 7 is a ladder diagram that depicts a periodic attempt to restore the ADI/R operation during sustained DDD/R operation.

FIG. 6 is a ladder diagram that depicts the pacing operation in the event that the patient develops AV block for more than one cycle. Note that according to the preferred embodiment of the present invention, a single missed beat (i.e., no Vs) will not by itself cause a mode switch, particularly if relatively reliable AV conduction is present. Following a mode switch to DDI/R, VA interval 9 times out, resulting in atrial paced event 1. A very long (e.g. 400 millisecond or up to approximately 70% of the median V-V interval) 17 may be used in an attempt to promote native AV conduction (or a Vp stimulus may be withheld) as further described hereinbelow. If, however, AV interval 17 is not interrupted by a sensed, intrinsic R-wave, as is depicted in the first cycle (labeled ADI/R), the pacemaker immediately switches to the DDD/R mode. In the event that a sensed, intrinsic R-wave does occur, the device reverts to the ADI/R operation (not shown). The DDD/R operation, with the programmed AV interval, will be sustained until a sensed, intrinsic R-wave is detected, as further described herein. Periodic attempts to force restoration of the ADI/R operation may be performed (as depicted in FIG. 7). Mode switching to the DDI/R mode may occur in the event that a PVC is detected and in the event that that an atrial tachycardia is detected a mode switch to DDD/R pacing is preferred.

FIG. 7 is a ladder diagram that depicts a periodic attempt to restore the ADI/R operation during sustained DDD/R operation. As mentioned, the DDD/R mode may become the sustained mode of operation in the event that the patient develops a prolonged AV block, such as might occur with rate-dependent AV block or if the AV conduction become relatively unreliable. In such cases, the device may be programmed to revert to ADI/R 1 after a programmable number of DDD/R cycles. Then, the device looks for a ventricular sensed event, e.g., at 23 following atrial pace 1. In the event that a sensed, intrinsic R-wave is detected, the ADI/R operation is immediately resumed. In the absence of a ventricular sensed event, the device continues to operate in the DDD/R mode, as indicated in the third cycle of FIG. 7.

Figure 8:
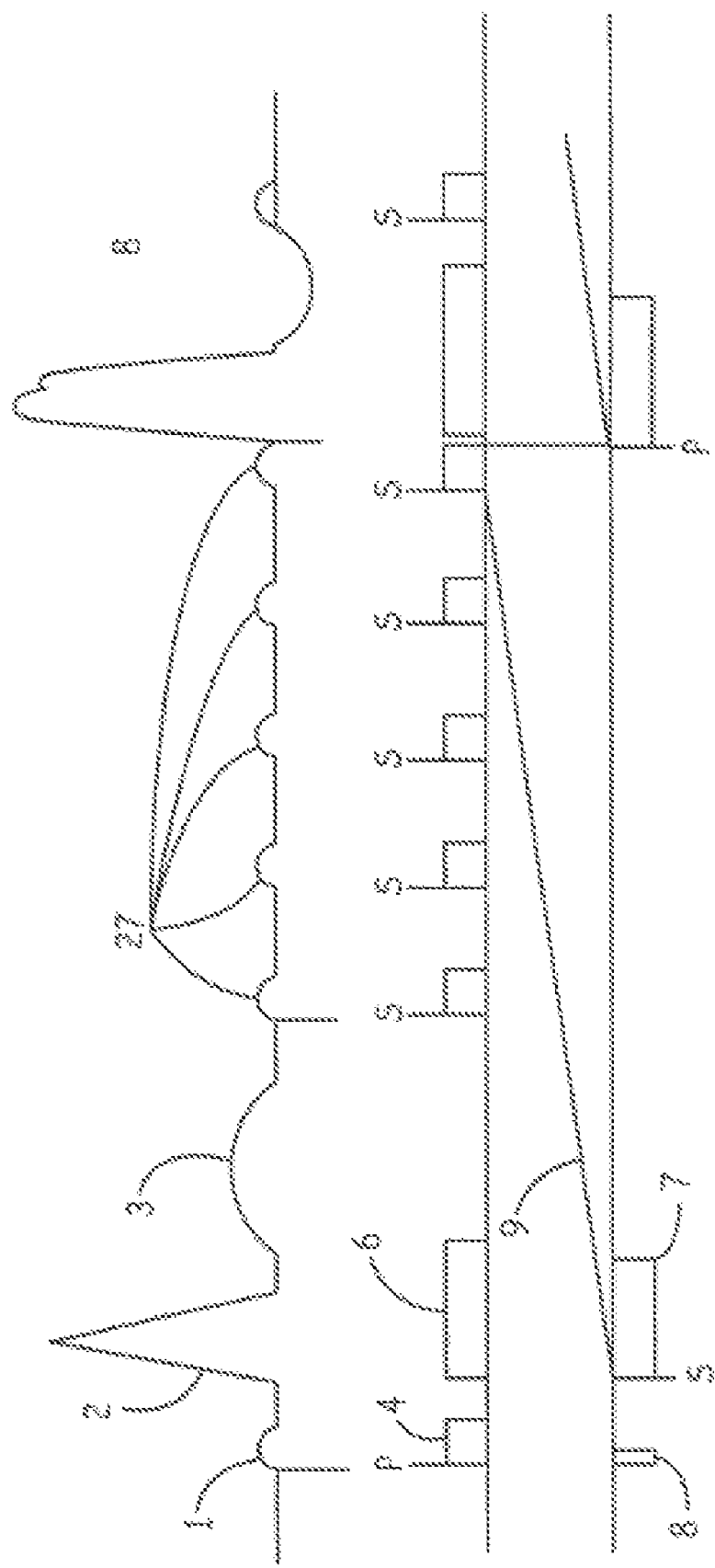
FIG. 8 is a ladder diagram of the pacing operation in the event that the patient develops an atrial tachycardia.

FIG. 8 is a ladder diagram of the pacing operation in the event that the patient 20 develops an atrial tachycardia. A sick sinus patient often has episodes of atrial tachycardia, atrial flutter, or atrial fibrillation. During these episodes, the pacing operation must be set such that the ventricular pacing rate will neither be synchronized to the fast atrial rate nor so slow as to cause symptoms. Preferably during episodes of AT, the atrial-based pacing ends and a DDD/R (or DDI/R) pacing mode is employed.

In FIG. 5 it was noted that the device, while operating in/mode also is well suited for pacing in the presence of an atrial tachycardia because it will not allow ventricular synchronization to a fast atrial rate nor will it allow the ventricular pacing rate to go below the programmed lower rate. Therefore, when an atrial tachycardia does occur, as shown in FIG. 8, fast atrial sensed events 27 without a conducted ventricular event have no effect on ventricular timing 9. Since there is no ventricular event, the operation immediately switches to the DDI/R mode. In the presence of an atrial tachycardia, the V-V interval 9 times out so that paced R-wave 8 will occur at the faster of the programmed lower rate or sensor-indicated rate in the DDI/R mode. The operation depicted in FIG. 8 will continue so long as the atrial tachycardia persists. Upon termination of the atrial tachycardia, the preferred ADI/R will resume as shown in FIG. 4 or 7, depending on how the heart recovers from the atrial tachyarrhythmia. If the atrial tachyarrhythmia terminates abruptly, the prompt restoration of the ADI/R mode may take place (see FIG. 4). If, however, the atrial tachyarrhythmia "cools down" slowly, there may be a period of DDD/R pacing with periodic attempts to restore ADI/R pacing as shown in FIG. 7.

Figure 9:
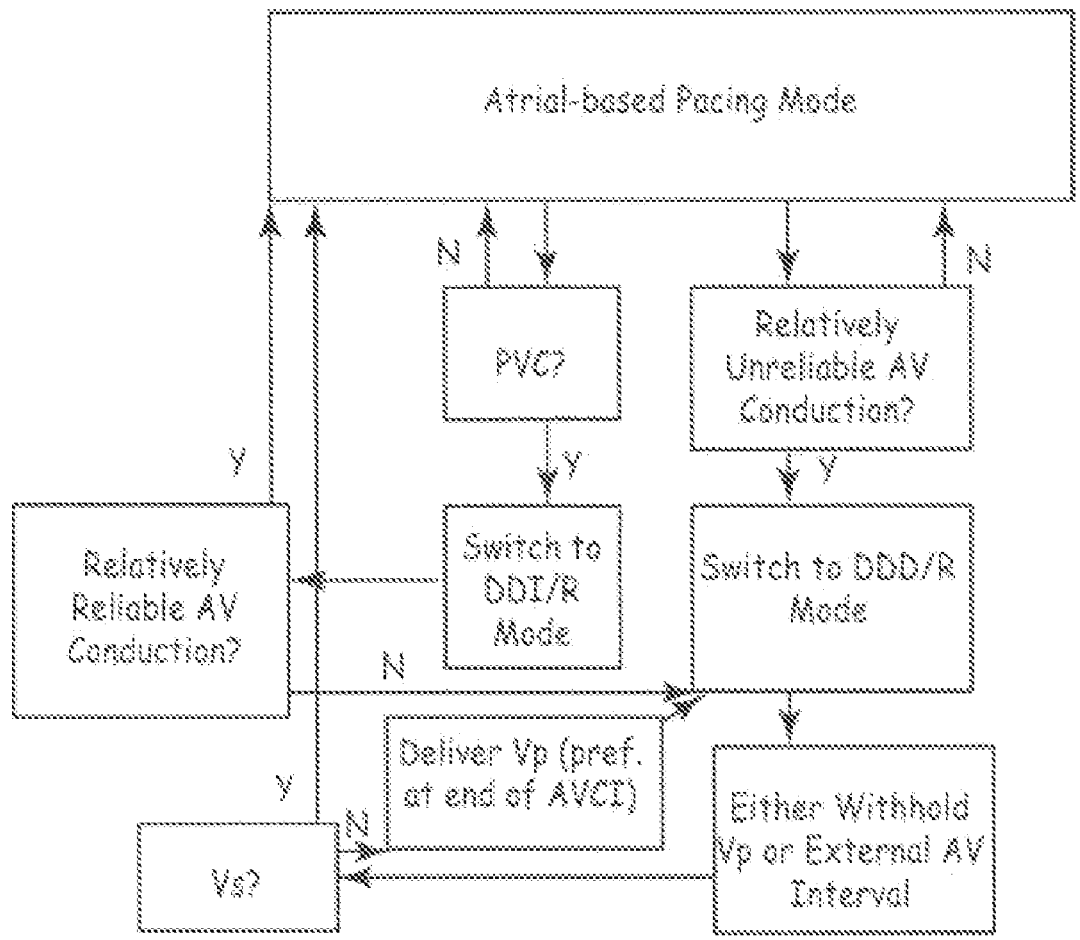
FIG. 9 is a flow chart illustrating one embodiment of a mode supervisor according to the present invention.

In contrast to a majority of the foregoing, and with general reference to FIG. 9, the MVP modality includes one or more of the following aspects.

Adaptive Atrial Refractory Period (ARP)

According to the initial definition of the preferred ADI/R modality, a rate-adaptive ARP is employed in order to distinguish physiologic atrial events from non physiologic events. According to a preferred implementation, an adaptive ARP is employed and defined as a fixed percentage of the physiologic interval (P1). One preferred method of determining the P1 is based on the ventricular rate as determined by the median R-R interval for the preceding 12 ventricular events (regardless if such events are sense- or pace-type events). Specifically the median value is determined algorithmically as the seventh longest interval of the preceding 12 R-R (i.e., V-R, RV, or V-V) intervals. Therefore, recalculation of the P1 occurs following event ventricular event as a new interval is added to a 12 beat accumulator (e.g., temporary memory structure) and the oldest is eliminated according on a FIFO (first-in, first-out) basis. Of course, a beat-to-beat instantiation may be used in lieu of the multi-beat techniques described herein.

The preferred implementation defines ARP as a programmable, fixed percentage of the P1. A suggested default value is seventy percent (70%) of the R-R interval (either a calculated value—such as a median value—or a beat-to-beat value derived from a prior R-R interval). Thereby, intrinsic atrial events that occur at regular intervals (consistent with a patient's current physiologic state) that fall outside of the ARP can be defined as physiologic while those within the ARP can be assumed to represent noise or are otherwise not physiologic. Alternatively, the ARP can be implemented as an adaptive approach with a fixed, absolute time period (i.e., fixed period of time maintained for the remainder of the P1). The philosophy behind the latter approach is for avoidance of atrial competitive pacing during the physiologic refractory period of the atrium. One possible downside of a fixed (e.g., 300 ms) alert period outside of the ARP, however, is the increased risk of misclassifying non 5 physiologic atrial events as physiologic.

Mode Supervisor:

The Wenckebach supervisor (as briefly described previously) has been renamed the "mode supervisor" because the mode supervisor can control a wide range of operations related to mode changes. The primary intent of the mode supervisor is to monitor a patient's atrioventricular status and intervene when necessary by invoking sustained mode-switches to conventional modes of pacing (i.e. DDD/R and DDI/R). According to the preferred implementation, the mode supervisor defines unreliable AV conduction according to a Wenckebach pattern with definition of a critical AV conduction acceptance ratio to discriminate between tolerable (or "relatively reliable") AV conduction states from intolerable (or "relatively unreliable") AV conduction states. For instance, an AV conduction acceptance ratio of 4:3 allows preferred ADI/R operation to persist as long as there are at least three ventricular events for every four physiologic atrial events. Should AV conduction falter such that the ratio of A to V events falls below the pre-defined acceptance ratio, a sustained switch to conventional DDD/R pacing will occur. Importantly, atrial events classified as non-physiologic (i.e. within the ARP) are not accounted for in the calculation of the A:V ratio. Thereby, inappropriate mode-switches to DDD/R are avoided in the presence of frequent non-conducted premature atrial contractions (PAC).

Upon invoking DDD/R pacing in the presence of unreliable AV conduction, the mode supervisor immediately assumes the role of striving to restore preferred ADI/R pacing. Since it is known that AV conduction disease typically progresses gradually with brief manifestations of high degree block expected in the early stages of disease progression, the mode supervisor will attempt to restore preferred ADI/R operation following only a brief episode of new onset DDD/R pacing. According to the preferred operation, the first reattempt to reveal intact AV conduction and to restore ADI/R pacing will occur only after a short period of time (e.g., one minute) of DDD/R pacing. Should ADL'R restoration fail, reattempts will be attempted at 2, 4, 8, 16 and 32 minutes and subsequently at 1, 2, 4, 8, 12 and 24 hours. Of course, other timing sequences may be used, both periodic and aperiodic (as well as local and remote clinician- or patient-activated atrial-based pacing initiation).

The algorithm used to search for intact AV conduction and restore ADI/R is defined according to one of two options. The first option is to simply withhold a ventricular pace stimulation during DDD/R operation. In the event that a ventricular sense follows the physiologic atrial event during which ventricular pacing was withheld, ADI/R pacing is resumed. Otherwise, DDD/R pacing continues with subsequent reattempts according to a schedule or by way of manual activation (as specified above). The second option searches for intact AV conduction involves extending the AV delay during DDD/R pacing to a pre-designated AV conduction [search] interval (AVCI). For instance, with an AVCI of 400 ms, the AV delay is extended to 400 ms following a physiologic atrial event (sensed or paced). In the event that the AV interval is interrupted by a ventricular sense, thereby preempting the ventricular pace in DDD/R operation, the mode supervisor reverts to ADI/R operation. Otherwise, a ventricular pace is delivered upon the expiration of the AVCI interval and DDD/R operation resumes with reattempts according to the schedule (or with manual activation) as described above. Importantly, in the event of failed conduction and ventricular pacing during these AV conduction search methods, an extended post-ventricular atrial refractory period (PVARP) in invoked following the AVCI in order to guard against the possibility of retrograde conduction initiating a pacemaker mediated tachycardia.

A third responsibility of the mode-supervisor is to recognize sustained pathologic atrial rhythms and to invoke sustained mode-switching to DDI/R pacing for the duration of the atrial tachyarrhythmia (AT). It is expected that the defining AT criteria will be consistent with that used by conventional pacing modes (e.g. 4 of 7 short A-A intervals) and that mode-switching operation will not be unique to the minimum ventricular pacing (MYP) modality and therefore is not further described in this disclosure. The uniqueness of the implementation within MVP lies in the possibility that mode-switching to DDI/R will occur either from the ADI/R or DDD/R operating states. The inventors believe that the notion of switching to/from DDI/R is novel, and although not practically necessary as ADI/R is not an atrial tracking mode, there may be some merit to switching directly to DDI/R in order to avoid an inadvertent switch to DDD/R in the event of transient conduction block during an AF event. Moreover, a sustained switch to DDI/R may be justified in order to provide some degree of rate-regularization during AF with an irregular ventricular response.

A fourth responsibility of the mode supervisor is to monitor for rapid repeated switches between preferred ADI/R and DDD/R pacing modes. If the device repeatedly switches back and forth between these modes every minute or every two minutes (e.g., or other relatively short period of time) the mode supervisor can suspend testing for AV conduction and allow the device to remain in DDD/R pacing, for example by setting the AV conduction testing interval to some number of hours (e.g. 2, 4, 8, 16). The number of repeated mode changes required to trigger such behavior remains to be determined and may be programmable.

A fifth responsibility of the mode supervisor is to monitor for repeated failed AV conduction tests at maximal test duration. So for example, if seven straight tests for AV conduction fail at 16 hour intervals, the mode supervisor can suspend AV conduction testing and the device can then remain in the DDD/R mode indefinitely.

A sixth responsibility of the mode supervisor involves suspending AV conduction testing based on physiologic parameters (rather than indefinitely terminating searches or simply suspending for a fixed number of hours or other period of time). For example, the mode supervisor can monitor heart rate and recognize that repeated switching back and forth between preferred ADI/R and DDD/R is associated with high heart rates (HR) or activity, and suspend AV conduction testing until the HR returns below a preset or dynamically set HR threshold. Similar functionality can be implemented in the case of rapid repeated switching associated with just low heart rates.

A seventh responsibility of the mode supervisor relates to varying the tolerated Wenckebach threshold dependent on the time of day or a signal from a sleep indicator. For example, in patients with known incidence of Wenckebach during sleep, the supervisor changes the threshold to tolerate more severe Wenckebach at that time in response to a positive indication that the patient has entered a sleep state or simply as a matter of timing (e.g., increase Wenckebach tolerance during expected sleep time of the patient).

An eighth responsibility of the mode supervisor involves maintaining a record of the sensor driven atrial paced rate at which the Wenckebach threshold was exceeded during ADI/R operation (thereby causing a mode switch to DDD/R). Subsequently, the upper sensor rate is thus restricted to not encourage high rate sensor driven pacing above rates at which reliable AV conduction does not exist. This operation, in essence, is a dynamic upper sensor rate that adapts according to information obtained during mode excursions from ADI/R to DDD/R.

A ninth responsibility of the mode supervisor relates to controlling the pacing mode of an ICD following delivery of a defibrillation therapy to the patient (i.e., high voltage shock delivery). In this aspect of the invention, the mode supervisor initiates ADI/R pacing with a DDI sequence, or in the ADI/R mode at a premature timing interval following delivery of a defibrillation therapy (i.e., a high voltage shock) in order to prevent a significant delay in delivery of a ventricular pace (Vp) in the event of transient post-shock AV block. Alternatively, a preferred option favors DDD/R pacing and delays resumption of ADI/R pacing for a pre-specified period of time following delivery of such a high voltage defibrillation shock.

PVC Response

According to ADI/R operation, premature ventricular contractions (PVC) will 20 not alter the timed delivery of the ensuing atrial pace. Since this can conceivably result in a closely coupled conducted ventricular event due to atrial pacing coincident or soon following a PCV, the inventors decided to deviate from ADI/R operation in this circumstance, in some embodiments, and effectively operate in a DDI/R modality. In doing so, following a PVC event the ensuing atrial pace is delayed and scheduled according the operating AV delay (preferably equal to the P1 minus 80 ms). In addition to providing more appropriate rhythm responses during bradycardia pacing operation interrupted by PVCs, the added advantage of having this PVC response is that asynchronous atrial pacing is avoided during runs of ventricular tachycardia. This has especially important implications for tachyarrhythmia control devices, which typically require consecutive detected VT intervals, as withholding atrial pacing during VT also removes the potentially interfering cross-chamber ventricular blanking periods that occur with atrial pacing.

Various aspects of certain embodiments of the present invention can be implemented using executable software code and/or operational parameters saved by (or downloaded to) a medical device. Such a device may be disposed in vivo and later programmed according to the invention or may be programmed prior to implantation (e.g., using firmware that may be reprogrammed or modified using telemetry techniques and the like). This is in contrast to a beat-to-beat implementation of the invention, which would preferably be implemented in hardware as understood by those of skill in the art. However, the present invention is not limited to only firmware or hardware implementations; indeed, the present invention may be implemented in a hybrid or combined in any desirable manner using device programming techniques known and used in the art. For clarity, however, the inventors specifically provide and herein claim a beat-to-beat instantiation of the present invention wherein the operation of the MVP modality is invoked for every beat on a beat-to-beat basis.

Referring to FIGS. 10A and 10B, the above referenced MVP protocols will generally handle cross talk and PVC's in the following manner. In FIG. 10A, an atrial pace is delivered during interval 1 and an atrial blanking period ABP or similar window is defined. Typically, such a window is on the order of about 80 ms but may be defined as desired. Any ventricular event, whether intrinsic or far-field is ignored if it occurs during the ABP. Thus, during interval 2 a PVC occurs within the ABP and is ignored. Despite there having been an intrinsic, conducted ventricular event the protocol considers interval 2 to be devoid of ventricular activity. Depending upon the embodiment of MVP, ventricular pacing is provided in interval 3 and in subsequent intervals until a conduction check occurs, a ventricular pace is inhibited, or another event occurs to switch the device back to the atrial based mode. In other words, despite there being intrinsic conduction present, ventricular pacing is provided; thus, reducing the efficiency of MVP in eliminating as much ventricular pacing as possible.

FIG. 10B illustrates cross talk or far field sensing of the atrial pace that is sensed by the ventricular lead and indicated on the ventricular channel during the ABP. As these events are ignored, this will have no effect on the MVP. Furthermore, the ABP is successful in preventing such cross talk from being misinterpreted. In other words, in this instance the ABP is performing its intended function and does not negatively affect the protocol for minimizing or reducing ventricular pacing. Thus, while cross-talk is appropriately handled, PVC's or other intrinsic ventricular events that occur during the ABP reduce the efficiency.

To avoid this reduction in efficiency, the present invention provides "feed back" or "feed forward" cross talk filtering protocols that are implemented with MVP. It is understood that there are many embodiments of MVP and that each will tolerate or react to missed ventricular beats in a variety of ways. The following description is meant to apply to any of these embodiments, though each variation is not separately described in detail.

Figure 11A:
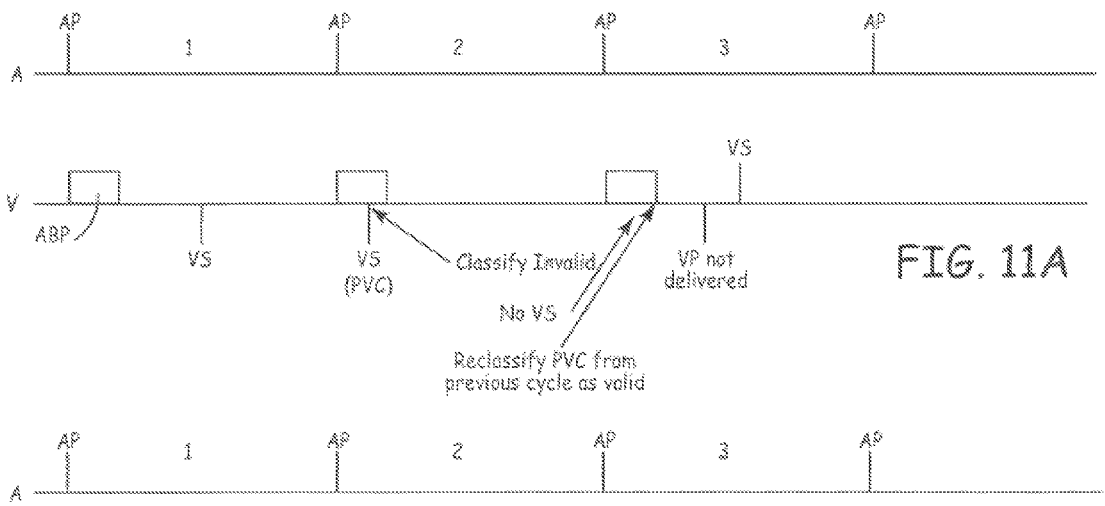
FIGS. 11A-11B are ladder diagrams that illustrate ventricular sense events during an ABP, while utilizing a feed back protocol.

FIG. 11A illustrates an embodiment using a "feed back" cross talk filtering protocol to address this situation. Under the "feed back" protocol, an event sensed in the ABP during an interval is classified as invalid, and hence ignored. This classification information is stored in hardware, software, firmware, or memory as a marker or other indicator. The ABP of the subsequent cycle (e.g., 3) is monitored. If there is a similar sense during this ABP, then the earlier classification is maintained. If there is no similar sense during the ABP then the earlier event is "reclassified" as a valid ventricular event and treated as such by the MVP algorithm. For example, in interval 2, a PVC occurs during the ABP. Initially, this is classified as invalid. During the next interval 3, there is no sensed event during the ABP and at the expiration of the ABP the previous PVC is reclassified as valid. Thus, interval 2 is indicated to have intrinsic ventricular conduction as of the expiration of the ABP in interval 3. As such, no ventricular pacing is provided during interval 3. From this point forward, operation continues normally under MVP.

In practice, this reclassification can be implemented in any number of ways. For example, if MVP is utilizing actual mode switching, the appropriate mode switch (assuming no ventricular sense in interval 2) could occur at the atrial pace for interval 3 with a subsequent mode switch (either actual or effective) at the expiration of the ABP. Alternatively, the mode switch to the dual chamber mode could be set to occur only after the ABP if there is no reclassification. Additionally, utilizing flags would include setting an appropriate flag after the ABP with the subsequent functionality resulting. As all of this occurs in the interval of interest, various ad hoc or single interval steps may be taken to address the implications of the short timeline leading to a return to normal MVP operation.

Figure 11B:
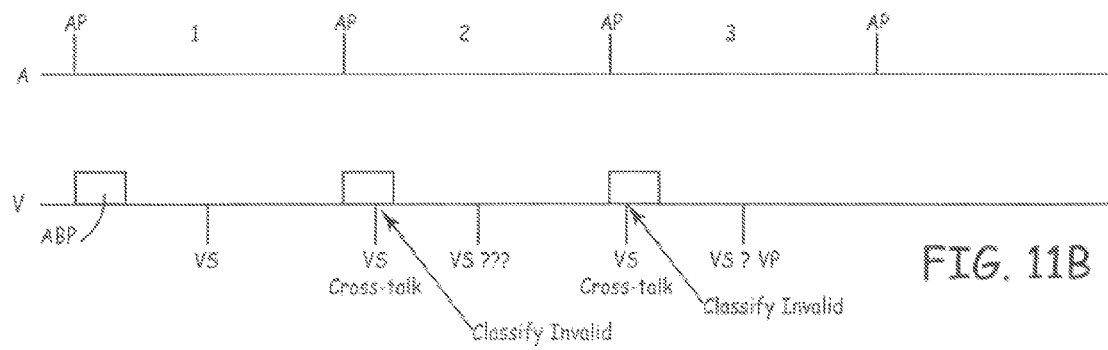

FIG. 11B illustrates a case where cross talk occurs during the ABP of interval 2. Again, since this is the first occurrence this ventricular sense is classified as invalid. During the subsequent ABP which occurs in interval 3, far field sensing will most likely occur again and is illustrated as such. Therefore, the ventricular sense of interval 2 is not reclassified, but rather remains invalid and ignored. MVP will function based upon whether or not ventricular events are sensed outside of the ABP.

Under extremely rare circumstances, this may lead to short term anomalous behavior that is either tolerated or in some embodiments addressed. It is conceivable (FIG. 11B) that far field sensing occurs only during interval 2 and the sensed event in interval 3 is actually a PVC or other intrinsic event. One option is to simply ignore this extremely unlikely scenario and simply treat the PVC as a far field sense. Another option would be to scrutinize the timing within the ABP of the various ventricular sensed events. Far field sensing should have predictable timing; thus, a PVC may fall within the ABP but have sufficiently different timing to distinguish this event so as to either reclassify the event of interval 2 (erroneously) or cause the event of interval 3 to be evaluated differently in intervals 4 and beyond. In other words, timing may be used to further distinguish ventricular senses during the ABP from binary results to more analytical results to distinguish between events when cross talk and PVC's are occurring. Furthermore, if far field sensing occurs along with and is separately distinguishable from a PVC during the ABP, this could also be used to indicate that intrinsic conduction is present along with cross talk.

Figure 12A:
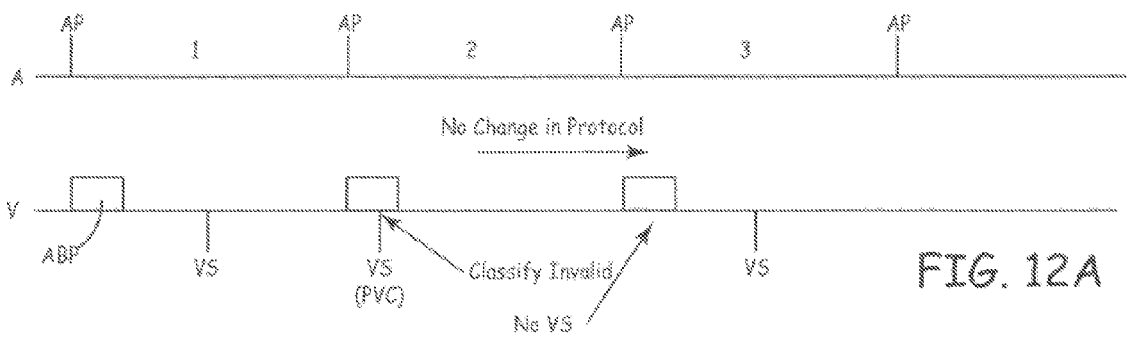
FIGS. 12A-12B are ladder diagrams that illustrate ventricular sense events during an ABP, while utilizing a feed forward protocol.
Figure 12B:
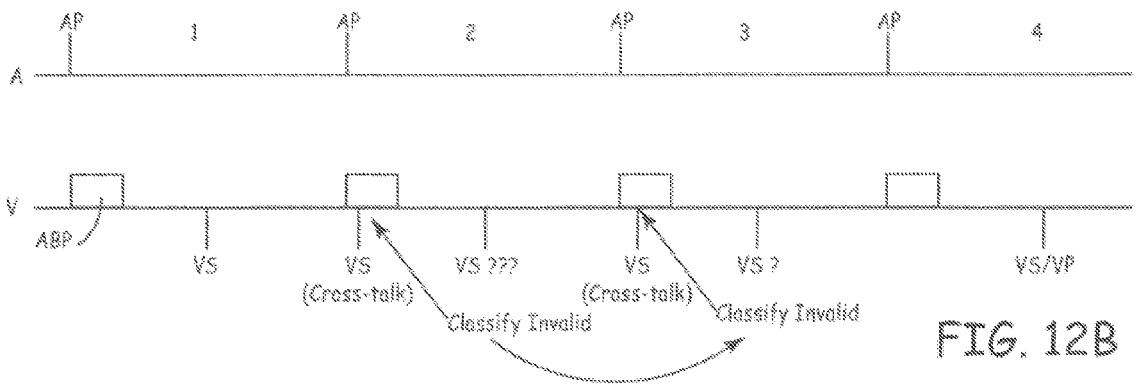

FIGS. 12A and 12B illustrate a "feed forward" cross talk filtering protocol for addressing sensed events during the ABP. In FIG. 12A, a PVC occurs during the ABP of interval 2. In this protocol, the first occurrence of such an event is classified as valid; in other words, it is considered an intrinsic, conducted event. Moving forward in time, MVP will behave normally from that point on. Thus, any sensed event on the ventricular channel is treated as a valid by MVP, regardless of when it occurs during the interval. While providing the desired results in the efficiency of MVP, this alone would simply be equivalent to eliminating the ABP and would leave open the problems associated with far field sensing or cross talk.

FIG. 12B illustrates how this problem is addressed. Here, the ventricular sense during the ABP of interval 2 is cross talk. As indicated, this occurrence is classified or considered as a valid ventricular event. Thus, whether or not an intrinsic ventricular depolarization occurs during interval 2, the MVP protocol acts as if it has. The classification of this event during the ABP as valid is "fed forward" and affects subsequent senses during the ABP. In this example, cross talk is sensed during the ABP of interval 3. The "fed forward" indicator has been toggled and this sense during the ABP of interval 3 is classified as invalid. Assuming cross talk is sensed during subsequent ABPs, those events will also be considered invalid. Thus, only a ventricular sense occurring outside of the ABP will satisfy the MVP protocol in interval 3 and beyond.

This may be a one-time toggle with an assumption that once cross talk is sensed, it will remain an issue until manually changed or corrected. Alternatively, the protocol may include provisions to reset itself if a predetermined number of intervals transpire without sensed activity during the ABP. This will automatically address intermittent cross talk. The predetermined number of intervals may be fixed or vary. That is, for the first occurrence, the system may reset after a few intervals but if cross talk is observed with some frequency, then attempts to reset are made less frequent and/or eliminated.

Similarly to the "feed back" protocol, the "feed forward" protocol conceptually permits some extremely unlikely anomalous behavior. First, PVCs may occur in consecutive cycles and be misinterpreted as cross talk. One solution is the automatic and/or periodic reset indicated above. Another option is to monitor the timing of the event within the ABP. True far field sensing should be somewhat stable and predictable. Thus, if the sensed events vary in time within the ABP by more that a predetermined percentage, these events may be reclassified as PVCs or at least subjected to a higher level of evaluation. Similarly, both far field sensing and PVCs could be present. This is simply solved by applying the above classifications, but if multiple events occur during a single ABP consider one to be an intrinsic ventricular event, subject to the remaining protocol parameters.

An even more remote scenario could occur in that a patient has intrinsic conduction and no cross talk for some period of time, e.g., up through interval 1 of FIG. 12B. Then, during the ABP of interval 2, a far field sense occurs. As indicated, with the "feed forward" protocol, this far field sense is classified as valid. In the same interval, the patient's conduction fails and there is no intrinsic ventricular activity. However, since the far field sense is classified as valid, the MVP protocol considers interval 2 to have a ventricular event. Subsequently, in interval 3, an atrial pace AP is delivered. During this ABP there could be another far field sense, which is classified as invalid due to the "feed forward" indicator. Again, assuming conduction block has occurred there is no intrinsic conduction; thus, there is no ventricular depolarization. At the conclusion of interval 3, the MVP protocol will recognize the absence of conduction and respond accordingly. Typically, this means providing a ventricular pace. However, in some embodiments, the mode supervisor MS may seek to have more than one interval out of a predetermined number of intervals without ventricular activity. Since, interval 3 was the first interval considered to be devoid of ventricular activity, the mode supervisor MS could permit interval 4 to transpire without ventricular pacing. Thus, it would be conceivable to have two or even three intervals without ventricular activity.

There are several ways to address this issue. The first is to realize that the likelihood of initiating far field sensing and loosing intrinsic conduction during the same cycle are miniscule. Even if this were to result, the effect on the patient would be tolerable and pacing would result in the third or fourth interval. Thus, while conceptually possible, the practical likelihood and results render this issue essentially moot.

To prevent even the chance of this occurring, certain steps may be taken. For example, only certain embodiments of the mode supervisor MS will permit a situation where three intervals could conceivably transpire without ventricular activity. Thus, one option is to not use this aspect of the mode supervisor protocol with the "feed forward" protocol.

Another option is to utilize portions of the "feed back" protocol with the "feed forward" protocol in certain circumstances. For example, the far field sense during the ABP of interval 2 is deemed valid. Because of this, the far field sense during the ABP of interval 3 is deemed invalid. When this condition occurs, the mode supervisor MS may then revisit the previous interval to determine if a second ventricular event occurred. If not, the validity of the interval 2 ABP sense may be reclassified.

It is to be understood that the above description is intended to be illustrative and, not restrictive. Many other embodiments will be apparent to those of skill in the art upon reading and understanding the above description. The scope of the invention should, therefore, be determined with reference to the appended claims, along with the full scope of equivalents to which such claims are entitled.

The invention claimed is:

1. A method of filtering far field sensing from intrinsic events occurring during an atrial blanking period that follows an atrial event, the method comprising:
    monitoring a ventricular channel during the atrial blanking period for a first interval;
    classifying a first sensed event on the ventricular channel during the atrial blanking period of the first interval as invalid;
    monitoring the ventricular channel during the atrial blanking period of a second interval, subsequent to the first interval; and
    reclassifying the first sensed event as valid if the atrial blanking period of the second interval transpires without a sense on the ventricular channel.

2. A method of filtering far field sensing from intrinsic events occurring during an atrial blanking period that follows an atrial event, the method comprising:
    monitoring a ventricular channel during the atrial blanking period for a first interval;
    classifying a first sensed event on the ventricular channel during the atrial blanking period of the first interval as valid;
    monitoring the ventricular channel during the atrial blanking period of a second interval, subsequent to the first interval; and
    classifying a second sensed event on the ventricular channel during the atrial blanking period of the second interval as invalid in response to the occurrence and classification of the first sensed event.

* * * * *